United States Patent
De Vries

(10) Patent No.: US 9,587,226 B2
(45) Date of Patent: Mar. 7, 2017

(54) METHOD FOR THE PRODUCTION OF RECOMBINANT POLYOMAVIRAL VECTOR PARTICLES

(75) Inventor: Walter Gerhardus De Vries, Leiden (NL)

(73) Assignee: Amarna Holding B.V., Leiden (NL)

( * ) Notice: Subject to any disclaimer, the term of this patent is extended or adjusted under 35 U.S.C. 154(b) by 1053 days.

(21) Appl. No.: 13/138,913

(22) PCT Filed: Apr. 22, 2010

(86) PCT No.: PCT/EP2010/055330
§ 371 (c)(1),
(2), (4) Date: Oct. 28, 2011

(87) PCT Pub. No.: WO2010/122094
PCT Pub. Date: Oct. 28, 2010

(65) Prior Publication Data
US 2012/0040399 A1    Feb. 16, 2012

(30) Foreign Application Priority Data
Apr. 22, 2009   (EP) .................................. 09158498

(51) Int. Cl.
| | |
|---|---|
| C12N 7/00 | (2006.01) |
| C12N 5/07 | (2010.01) |
| C12N 5/16 | (2006.01) |
| C12N 5/00 | (2006.01) |
| C12N 5/02 | (2006.01) |
| C12N 15/00 | (2006.01) |
| C12P 21/06 | (2006.01) |

(52) U.S. Cl.
CPC ...... *C12N 7/00* (2013.01); *C12N 2710/22051* (2013.01); *C12N 2710/22052* (2013.01)

(58) Field of Classification Search
CPC C12N 7/00; C12N 15/86; C12N 2750/14143; C12N 2710/22021; C12N 2710/22043; C12N 2720/12222; C12N 2730/10123; C12N 2730/10134; C12N 2740/16322; C12N 2770/38043; C07K 14/005; A61K 35/76
See application file for complete search history.

(56) References Cited

FOREIGN PATENT DOCUMENTS

| WO | WO 99/27123 | 6/1999 |
| WO | WO 03/025189 | 3/2003 |
| WO | 2005024030 A1 | 3/2005 |
| WO | WO 2008/000779 | 1/2008 |

OTHER PUBLICATIONS

Pyeon et al. Production of infectious human papillomavirus independently of viral replication and epithelial cell differentiation. Jun. 28, 2005, PNAS. vol. 102, No. 26, pp. 9311-9316.*
293TT. 293TT cells. Laboratory of Cellular Oncology. Printed on Sep. 28, 2014, 5 pages.*
Gauchat, et al.; On the functional roles of simian virus 40 large and small T0antigen in the induction of a mitotic host response; Nucleic Acids Research; Dec. 9, 1986; vol. 14, No. 23; pp. 9339-9351.
Khoury, et al.; Processing and expression of early SV40 mRNA: a role for RNA conformation in splicing; Cell; vol. 18, No. 1; Sep. 1, 1979; pp. 85-92.
PCT International Written Opinion and Search Report PCT/EP2010/055330 dated Jun. 25, 2010, 10 pages.
Sun, et al; Tumorigenic study on hepatocytes coexpressing SV40 wilt Ras.; Molecular Carcinogenesis; Apr. 2006; vol. 45, No. 4 pp. 213-219.
PCT International Preliminary Report on Patentability, PCT/EP2010/055330 dated Oct. 25, 2011, 6 pages.
Brown et al., A Recombinant Murine Retrovirus for Simian Virus 40 Large T cDNA Transforms Mouse Fibroblasts to Anchorage-Independent Growth, Joural of Virology, Oct. 1986, pp. 290-293, vol. 60, No. 1.
Gerard et al., New Host Cell System for Regulated Simian Virus 40 DNA Replication, Molecular and Cellular Biology, Nov. 1985, pp. 3231-3240, vol. 5, No. 11.
Vera et al., Factors Influencing the Production of Recombinant SV40 Vectors, Molecular Therapy, Oct. 2004, pp. 780-791, vol. 10, No. 4.
Zhang et al., Activation of the Tumor-Specific Death Effector Apoptin and Its Kinase by an N-Terminal Determinant of Simian Virus 40 Large T Antigen, Journal of Virology, Sep. 2004, pp. 9965-9976, vol. 78, No. 18.

* cited by examiner

Primary Examiner — Catherine S Hibbert
Assistant Examiner — Channing S Mahatan
(74) *Attorney, Agent, or Firm* — TraskBritt, P.C.

(57) ABSTRACT

The present invention relates to improved methods for the production of viral particles, viral vector particles and recombinant proteins. In particular, the invention relates to improved methods for the production of recombinant polyomaviral vector particles and polyomaviral vector production cell lines. More in particular, the invention relates to methods for the production of simian polyomaviral vector particles such as simian virus 40 (SV40) viral vector particles. The invention also relates to compositions comprising viral vectors and uses thereof and viral vector particles to treat genetic disorders, transplant rejection, autoimmune diseases, infectious diseases, allergies or cancer. The invention also relates to methods for the production of recombinant proteins in mammalian cells and methods to enhance the production of recombinant proteins in mammalian cells.

11 Claims, No Drawings

SEQUENCE LISTING

<160> NUMBER OF SEQ ID NOS: 27

<210> SEQ ID NO 1
<211> LENGTH: 43
<212> TYPE: DNA
<213> ORGANISM: Artificial Sequence
<220> FEATURE:
<223> OTHER INFORMATION: Probes and primers

<400> SEQUENCE: 1
ccgctcgagt tgcggccgct gtgccttcta gttgccagcc atc         43

<210> SEQ ID NO 2
<211> LENGTH: 34
<212> TYPE: DNA
<213> ORGANISM: Artificial Sequence
<220> FEATURE:
<223> OTHER INFORMATION: Probes and Primers

<400> SEQUENCE: 2
ggtaccatag agcccaccgc atccccagca tgcc         34

<210> SEQ ID NO 3
<211> LENGTH: 52
<212> TYPE: DNA
<213> ORGANISM: Artificial Sequence
<220> FEATURE:
<223> OTHER INFORMATION: Probes and Primers

<400> SEQUENCE: 3
ggccgcttta ttaattaagc cctgcaggtt gtttaaactt ggcgcgcctt at         52

<210> SEQ ID NO 4

```
<210> SEQ ID NO 4
<211> LENGTH: 50
<212> TYPE: DNA
<213> ORGANISM: Artificial Sequence
<220> FEATURE:
<223> OTHER INFORMATION: Probes and Primers

<400> SEQUENCE: 4
cgataaggcg cgccaagttt aaacaacctg cagggcttaa ttaataaagc          50

<210> SEQ ID NO 5
<211> LENGTH: 28
<212> TYPE: DNA
<213> ORGANISM: Artificial Sequence
<220> FEATURE:
<223> OTHER INFORMATION: Probes and Primers

<400> SEQUENCE: 5
cgggatccag acatgataag atacattg                                  28

<210> SEQ ID NO 6
<211> LENGTH: 42
<212> TYPE: DNA
<213> ORGANISM: Artificial Sequence
<220> FEATURE:
<223> OTHER INFORMATION: Probes and Primers

<400> SEQUENCE: 6
atagtttagc ggccgcaact tgtttattgc agcttataat gg                  42

<210> SEQ ID NO 7
<211> LENGTH: 40
<212> TYPE: DNA
<213> ORGANISM: Artificial Sequence
<220> FEATURE:
<223> OTHER INFORMATION: Probes and Primers

<400> SEQUENCE: 7
ttggcgcgcc atggaagacg ccaaaaacat aaagaaaggc                     40

<210> SEQ ID NO 8
<211> LENGTH: 36
<212> TYPE: DNA
<213> ORGANISM: Artificial Sequence
<220> FEATURE:
<223> OTHER INFORMATION: Probes and Primers

<400> SEQUENCE: 8
cccttaatta attacacggc gatctttccg cccttc                         36

<210> SEQ ID NO 9
<211> LENGTH: 27
<212> TYPE: DNA
<213> ORGANISM: Artificial Sequence
<220> FEATURE:
<223> OTHER INFORMATION: Probes and Primers

<400> SEQUENCE: 9
gggatccaga catgataaga tacattg                                   27

<210> SEQ ID NO 10
<211> LENGTH: 44
<212> TYPE: DNA
<213> ORGANISM: Artificial Sequence
<220> FEATURE:
<223> OTHER INFORMATION: Probes and Primers

<400> SEQUENCE: 10
```

```
atagtttagc ggccgcaatg aatgcaattg ttgttgttaa cttg          44

<210> SEQ ID NO 11
<211> LENGTH: 51
<212> TYPE: DNA
<213> ORGANISM: Artificial Sequence
<220> FEATURE:
<223> OTHER INFORMATION: Probes and Primers

<400> SEQUENCE: 11
gccgctttat taattaagcc ctgcaggttg tttaaacttg gcgcgcctta t     51

<210> SEQ ID NO 12
<211> LENGTH: 50
<212> TYPE: DNA
<213> ORGANISM: Artificial Sequence
<220> FEATURE:
<223> OTHER INFORMATION: Probes and Primers

<400> SEQUENCE: 12
cgaaataatt aattcgggac gtccaacaaa tttgaaccgc gcggaatagc        50

<210> SEQ ID NO 13
<211> LENGTH: 14
<212> TYPE: DNA
<213> ORGANISM: Artificial Sequence
<220> FEATURE:
<223> OTHER INFORMATION: Probes and Primers

<400> SEQUENCE: 13
cggcggccgc gtac                                              14

<210> SEQ ID NO 14
<211> LENGTH: 43
<212> TYPE: DNA
<213> ORGANISM: Artificial Sequence
<220> FEATURE:
<223> OTHER INFORMATION: Probes and Primers

<400> SEQUENCE: 14
ttggcgcgcc tcaatattgg ccattagcca tattattcat tgg              43

<210> SEQ ID NO 15
<211> LENGTH: 44
<212> TYPE: DNA
<213> ORGANISM: Artificial Sequence
<220> FEATURE:
<223> OTHER INFORMATION: Probes and Primers

<400> SEQUENCE: 15
gctaggtcgg aggcgccggc ccttgccacg taaccttcga acag             44

<210> SEQ ID NO 16
<211> LENGTH: 38
<212> TYPE: DNA
<213> ORGANISM: Artificial Sequence
<220> FEATURE:
<223> OTHER INFORMATION: Probes and Primers

<400> SEQUENCE: 16
ccacccaagc ttatgaccga gtacaagccc acggtgcg                    38

<210> SEQ ID NO 17
<211> LENGTH: 38
<212> TYPE: DNA
```

<213> ORGANISM: Artificial Sequence
<220> FEATURE:
<223> OTHER INFORMATION: Probes and Primers

<400> SEQUENCE: 17
cgtactgggc gttcgggcca cggactgagc tcgcctat                           38

<210> SEQ ID NO 18
<211> LENGTH: 37
<212> TYPE: DNA
<213> ORGANISM: Artificial Sequence
<220> FEATURE:
<223> OTHER INFORMATION: Probes and Primers

<400> SEQUENCE: 18
caaccgctcg agctgtgcct tctagttgcc agccatc                            37

<210> SEQ ID NO 19
<211> LENGTH: 31
<212> TYPE: DNA
<213> ORGANISM: Artificial Sequence
<220> FEATURE:
<223> OTHER INFORMATION: Probes and Primers

<400> SEQUENCE: 19
cccctacgcc acccgagata ccccatgggg c                                  31

<210> SEQ ID NO 20
<211> LENGTH: 40
<212> TYPE: DNA
<213> ORGANISM: Artificial Sequence
<220> FEATURE:
<223> OTHER INFORMATION: Probes and Primers

<400> SEQUENCE: 20
accatggata aagttttaaa cagagaggaa tctttgcagc                         40

<210> SEQ ID NO 21
<211> LENGTH: 33
<212> TYPE: DNA
<213> ORGANISM: Artificial Sequence
<220> FEATURE:
<223> OTHER INFORMATION: Probes and Primers

<400> SEQUENCE: 21
ttatgtttca ggttcagggg gaggtgtggg agg                                33

<210> SEQ ID NO 22
<211> LENGTH: 53
<212> TYPE: DNA
<213> ORGANISM: Artificial Sequence
<220> FEATURE:
<223> OTHER INFORMATION: Probes and Primers

<400> SEQUENCE: 22
tcctgcaggc ggggtaccct agtctagact agccgcgggg agtttaaaca gct          53

<210> SEQ ID NO 23
<211> LENGTH: 53
<212> TYPE: DNA
<213> ORGANISM: Artificial Sequence
<220> FEATURE:
<223> OTHER INFORMATION: Probes and Primers

<400> SEQUENCE: 23
gtttaaactc cccgcggcta gtctagacta gggtaccccg cctgcaggag tac          53

```
<210> SEQ ID NO 24
<211> LENGTH: 34
<212> TYPE: DNA
<213> ORGANISM: Artificial Sequence
<220> FEATURE:
<223> OTHER INFORMATION: Probes and Primers

<400> SEQUENCE: 24
gcaggctacc atggataaag ttttaaacag agag                            34

<210> SEQ ID NO 25
<211> LENGTH: 55
<212> TYPE: DNA
<213> ORGANISM: Artificial Sequence
<220> FEATURE:
<223> OTHER INFORMATION: Probes and Primers

<400> SEQUENCE: 25
gaaacctccg aagaccctac gttgactcta aggttggata ccttgactac ttacc     55

<210> SEQ ID NO 26
<211> LENGTH: 56
<212> TYPE: DNA
<213> ORGANISM: Artificial Sequence
<220> FEATURE:
<223> OTHER INFORMATION: Probes and Primers

<400> SEQUENCE: 26
ctttggaggc ttctgggatg caactgagat tccaacctat ggaactgatg aatggg    56

<210> SEQ ID NO 27
<211> LENGTH: 33
<212> TYPE: DNA
<213> ORGANISM: Artificial Sequence
<220> FEATURE:
<223> OTHER INFORMATION: Probes and Primers

<400> SEQUENCE: 27
aggaatgttg tacaccatgc attttaaaaa gtc                             33
```

METHOD FOR THE PRODUCTION OF RECOMBINANT POLYOMAVIRAL VECTOR PARTICLES

CROSS-REFERENCE TO RELATED APPLICATIONS

This is a national phase entry under 35 U.S.C. §371 of International Patent Application PCT/EP2010/055330, filed Apr. 22, 2010, published in English as International Patent Publication WO 2010/122094 A1 on Oct. 28, 2010, which claims the benefit under Article 8 of the Patent Cooperation Treaty to European Patent Application Serial No. 09158498.7, filed Apr. 22, 2009.

FIELD OF THE INVENTION

The present invention relates to improved methods for the production of viral particles, viral vectors, viral vector particles and recombinant proteins. In particular, the invention relates to improved methods for the production of recombinant polyomaviral vector particles and polyomaviral vector producer cell lines. More in particular, the invention relates to methods for the production of simian polyomaviral vectors such as simian virus 40 (SV40) viral vectors. The invention also relates to compositions comprising viral vectors and uses thereof and viral vector particles to treat genetic disorders, transplant rejection, auto-immune diseases, infectious diseases, allergies or cancer. The invention also relates to methods for the production of recombinant proteins in mammalian cells and methods to enhance the production of recombinant proteins in mammalian cells.

BACKGROUND OF THE INVENTION

Over the last decade, much effort has been dedicated to the development of efficient gene or nucleic acid delivery technologies for introduction and proper expression of genes or nucleic acids in target cells. Therapeutic genes or nucleic acids can be used to restore malfunctioning genes to treat genetic disorders, to induce an immune response to treat cancer and infectious diseases or to suppress an immune response e.g. for inducing/restoring immune tolerance to prevent transplant rejection or to treat autoimmune diseases and allergies. The therapeutic genes or nucleic acids can be administered as naked molecules or as nucleic acids packaged in lipid and/or proteinaceous compounds.

Since viruses evolved to deliver and express their genetic information into their host target cells, viral vectors have been explored as gene delivery vehicles and were found to be by far the most effective means of delivering genetic information into a living cell. A number of viral vector gene delivery systems have been developed and tested in pre-clinical and clinical trials. These trials revealed that the currently used vectors, which are derived from adenoviruses, poxviruses, herpesviruses, alphaviruses, retroviruses, parvoviruses and polyomaviruses, are generally safe to use and efficient in delivering therapeutic genes to target cells.

A major disadvantage of the currently used viral gene delivery vectors is the fact that they cannot be produced in sufficient amounts to treat significant numbers of patients. The majority of viral vectors is produced by transfecting producer cells with plasmid DNA encoding the vector and the vector components. This generally yields 1 to 10 million vector particles per milliliter cell culture volume. In clinical trials, generally $1 \times 10^{10}$ to $1 \times 10^{12}$ vector particles have to be administered to a patient in order to accomplish beneficial clinical effects. This means that in order to treat 1000 patients, more than 1 million liters of cell culture are required to yield sufficient amounts of vector particles.

In addition, preclinical and clinical trials revealed that most of the tested viral gene delivery vectors such as adenoviral, poxviral, herpesviral, alphaviral and retroviral vectors induce a strong immune response in patients, directed to viral vector components and the therapeutic gene products. As a consequence these vectors can only be administered a single time to a patient, whereas the expression levels of the introduced therapeutic gene rapidly decline. Viral vectors derived from adeno-associated virus (AAV) do not induce immune responses in animals and are immunologically inert. However, the majority of the human population encountered wildtype AAV together with its helper virus, e.g. adenovirus and as a result developed a strong CTL memory against the AAV capsid proteins. As a consequence AAV-transduced cells are rapidly removed and the expression levels of the therapeutic gene or nucleic acid introduced by an AAV viral vector rapidly decline.

The yields of recombinant proteins produced in mammalian cells compared to those produced in prokaryote cells are in general low, despite the use of strong promoters and/or multicopy transgene insertions or other ways to enhance the transcription. Viral replication competent vectors or replicons have been used for a long time as expression systems for the production of recombinant proteins in mammalian cells. The target gene in such vectors can be expressed under transcriptional control of viral promoters whereby the desired mRNAs may accumulate to extremely high levels in the cytoplasm early after transfection, yielding large amounts of target protein. So far the successes with replicon-based expression systems have been limited. Replicon systems based on RNA viruses in general produce recombinant proteins for only a short period of time, whereas those derived from DNA viruses in general do not replicate well in the commercially used cell lines.

To our knowledge, there is only one viral gene delivery vector that is immunologically inert in humans and that can be produced in sufficient amounts to treat a significant number of patients. Moreover, this viral gene delivery vector can be employed as a replicon system for the production of recombinant proteins in mammalian cell lines. This viral vector system is derived from simian virus 40 (SV40), a simian polyomavirus.

Polyomaviruses are comprised of a family of non-enveloped DNA viruses with icosahedral capsids. They are isolated from a variety of animal species including humans, monkeys, rodents and birds. Five human polyomaviruses have been described, termed BK, JC, WU, KI and Merkel Cell polyomavirus. Many monkey polyomaviruses have been described of which SV40 is the most well-known. SV40 replicates poorly in human cells and infections in humans are rare. Occasional SV40 infections occurred through transmission of the virus from monkeys to people living in close contact with these animals or through vaccination with batches of inactivated poliovirus particles contaminated with SV40.

SV40 has a 5.25 kilo base pairs long circular double stranded DNA genome. The SV40 genome consists of two regulatory regions, the promoter/origin region and the polyadenylation region. The promoter/origin region is 500 base pairs long and comprises two oppositely-directed promoters, the early and late promoter (SVEP and SVLP respectively), the origin of replication and the packaging signal. The polyadenylation region is 100 base pairs long and contains the polyadenylation signals of both the early and the late transcripts. SVEP drives expression of the early primary transcript that is spliced by host-encoded splicing factors into 2 different mRNAs encoding small and large tumor (T) antigens.

The large T antigen is the replicase-associated protein required for DNA replication and for activation of the SVLP. Although the precise role of the small T antigen in virus replication has remained unclear, small T antigen is required for the transformation of several mammalian cell types, in conjunction with large T antigen. The primary effects of small T antigen occur through its interaction with serine-threonine protein phosphatase 2A. The phosphatase 2A-binding domain of small T antigen is located at the unique carboxy-terminal end of the small T antigen.

It is well documented in the prior art that both large T antigen and small T antigen are required for efficient polyomavirus replication (Fahrbach K. M. et al., Virology 370 (2): 255-263, 2008).

SVLP drives expression of the late primary transcript that is spliced by host-encoded splicing factors into different mRNAs encoding the viral capsid proteins VP1, 2 and 3. The T antigens are the major and the capsid proteins the minor immunogenic components of polyoma viruses, eliciting cellular and humoral immune responses against SV40-infected cells.

The SV40 T antigens cooperatively immortalize primary mammalian cells, transform established mammalian cell lines and induce tumours in immuno-compromized young-borne rodents. A number of reports suggest that SV40 infections are associated with human malignancies, caused by the oncogenic activity of the chronically expressed T antigens (Butel J. S. and Lednicky J. A. Journal of the National Cancer Institute 91: 119-134, 1999).

Since expression of the viral capsid proteins is dependent on the presence of the large T antigen, T antigen-specific sequences have been deleted in polyoma viral vectors, not only for rendering the vectors replication-incompetent, but also to completely eliminate their immunogenicity in humans.

T antigen-deleted polyoma viral vectors derived from SV40 have been made and tested, in which the therapeutic genes or nucleic acids are expressed in trans in target cells under transcriptional control of the viral SVEP. Said vectors are known for a long time as potential vectors for gene transfer into a plurality of human tissues and cell types, for example, bone marrow (Rund D. et al, Human Gene Therapy 9: 649-657, 1998), the liver (Strayer D. S. and Zern M. A., Seminars in Liver Disease 19: 71-81, 1999) and dendritic cells (Vera M. et al., Molecular Therapy 12: 950-959, 2005).

Polyomaviral vectors, such as SV40, are known to infect non-dividing as well as actively dividing cells. Since the vectors lack the region encoding the T antigens and as a consequence do not express the viral capsid proteins, they are non-immunogenic (Strayer D. S. and Zern M. A., Seminars in Liver Disease 19: 71-81, 1999) allowing repeated administration to the same individual. Moreover, since the inserted therapeutic gene constructs are expressed under transcriptional control of SVEP, a weak but constitutive promoter, said vectors induce long-term expression of the therapeutic proteins in vivo. Thus, it is known that polyomaviral vectors, such as SV40-derived vectors are promising candidates for therapeutic gene or nucleic acid transfer that can be used for the above mentioned applications.

Because of their replication potential, polyomavirus-based replicons are also of great interest to enhance the production of recombinant proteins such as antibodies, growth factors and hormones in mammalian cells.

T antigen-deleted SV40 particles have been produced in simian cells that are permissive for lytic growth of SV40 and that supply the T antigens in trans. SV40 vector packaging cell lines that are currently used are COS cell lines in particular COS-1 and COS-7 (Gluzman Y., Cell 23: 175-182, 1981). COS cell lines were generated by transformation of monkey CV1 cells with SV40 DNA. Another cell line that expresses the SV40 T antigen in trans is CMT4. The CV1-derived CMT cell lines were generated using SV40 DNA in which the T antigens were expressed under transcriptional control of the mouse metallothionein promoter (Gerard R. D. and Gluzman Y., Molecular and Cellular Biology 5: 3231-3240, 1985).

There is an important disadvantage however to the use of such cell lines. Passaging of T antigen-deleted SV40 vectors in the constructed packaging cell lines (COS or CMT) in many cases results in the appearance of wildtype replication-competent SV40 particles (Gluzman Y., Cell 23: 175-182, 1981; Oppenheim A. and Peleg A., Gene 77: 79-86, 1989; Vera M. et al., Molecular Therapy 10: 780-791, 2004).

This most likely occurs by nucleotide sequence homology-dependent recombination between the chromosomally inserted SV40-specific sequences and nuclear SV40 vector-specific sequences. The emergence of the replication competent wildtype virus particles and the presence of the T antigen oncoproteins in such conventional packaging cell lines have made the use of SV40 vectors for medical purposes impractical.

The human embryo kidney 293 (HEK293) cell line is semi-permissive to SV40 infection, which means that only a small percentage of infected cells support virus replication. The majority of cells are persistently infected and show very low levels of virus replication.

A derivative of the HEK293 cell line is the HEK293T cell line, expressing the SV40 early region under transcriptional control of the Rous sarcoma virus long terminal repeat promoter. It has been described that HEK293T cells express very low amounts of large T antigen and large amounts of small T antigen, due to a splicing bias in favour of the SV40 small T antigen mRNA. Vera et al. found that HEK293T poorly supports SV40 viral vector production (Vera M., et al., Molecular Therapy 10: 780-791, 2004).

Since the T antigen oncoproteins are present in HEK293T cells and there is a risk that replication competent SV40 viruses emerge, the use of this cell line for the production of SV40 vectors for medical purposes is undesired and impractical.

The HEK293TT cell line has been developed as a derivative of HEK293T, generated by stable transfection with a gene construct encoding the SV40 large T antigen. HEK293TT cells are used for the production of recombinant human papilloma virus (HPV) pseudo-vector particles. The recombinant HPV pseudo-vector particles are produced in HEK293TT by transfecting the cells with a plasmid that harbours the SV40 origin of replication and the HPV capsid genes and one that harbours the SV40 origin of replication and a HPV pseudo-genome (Buck C. B. et al., Methods in Molecular Medicine 119: 445-462, 2005).

Since HEK293TT as a derivative of HEK293T accumulates the small and large T antigen oncoproteins and poorly supports SV40 replication, the use of this cell line to produce recombinant SV40 vectors for medical purposes is also undesired and impractical.

WO 03/025189 describes packaging complementation cell lines that allow for the production of SV40 vector particles that are allegedly safe for medical use. However, the packaging cell lines described herein still accumulate significant amounts of the small and large T antigen oncoproteins.

Vera M. et al., Molecular Therapy 10: 780-791, 2004 showed that the production capacity of recombinant SV40 vector particles of interest in certain cell lines such as CMT4 and HEK293T can be very low and state that the cell lines described in WO 03/025189, such as COT-2 are also not effective as producer cell lines for the recombinant SV40 virus particles, possibly due to the splicing bias in favour of the small T antigen mRNA in these cell types.

WO 08/000779 describes a method to overcome the problem with the production of high titre stocks of suitable SV40 viral vectors using viral suppressors of RNA interference (RNAi), such as the vaccinia virus E3L and influenza A virus NS1 proteins. The packaging cell lines described in WO 08/000779 do not provide a solution to the disadvantages of the packaging cell lines of the prior art described herein above.

Chinese hamster ovary (CHO) cells have been provided with the mouse polyomavirus early region, resulting in CHOP cell lines (Heffernan and Dennis, Nucleic Acids Research 19: 85-92, 1991). A number of CHOP cell lines supported replication of plasmid CDM8 (invitrogen), a mammalian expression vector carrying the mouse polyomavirus origin of replication. The level of replication in the CHOP cell lines was not sufficient to make this system attractive for commercial application, possibly due to a splicing bias in favour of the small T antigen or middle T antigen mRNA in CHO cells.

There remains a desire in the art for efficient production systems for recombinant polyomavirus particles that are safe to use and yield high titers of viral vector particles. It is therefore an object of the present invention to provide methods for the safe and efficient production of polyomavirus particles and compositions obtainable therewith. It is appreciated that the methods of the present invention can also be used for the production of large amounts of recombinant proteins in mammalian cells.

SUMMARY OF THE INVENTION

The above objects have been met by the present invention in that a method is provided for producing recombinant polyomaviral vector particles incapable of expressing a functional small T antigen comprising the steps of a) providing a cell line permissive to the wildtype polyomavirus, said cell line being capable of expressing a functional large T antigen but incapable of expressing a functional polyomaviral small T antigen, b) introducing into said cell line a polyomavirus DNA incapable of encoding a functional small T antigen, c) culturing said cells in a growth medium under conditions allowing the formation of recombinant polyomaviral vector particles and d) harvesting the recombinant polyomaviral vector particles from the cell culture.

The recombinant polyomaviral vector particles produced by this method are incapable of expressing functional small T antigen and cannot revert into wildtype polyomavirus particles. This may be due to a complete lack of genes encoding a functional small T antigen, in the polyomaviral vector as well as in the polyomaviral vector producer cell line.

This now enables for the first time the preparation of a composition comprising a significant number of recombinant polyomaviral vector vector particles without a single wildtype polyomavirus particle. The viral vector particles produced in this method are unable to replicate in cells which are permissive for the wildtype polyomavirus and which do not express a functional large T antigen. Hence this composition is safe to use in medical treatments.

To date, it has not been possible to produce large quantities of polyomaviral vector particles, free of wildtype polyomavirus revertants or recombinants. With the use of the invention, it is now possible to obtain large quantities of uniform viral vector particles without a single wildtype virus being present. Accordingly, the invention relates to a composition comprising more than $10^6$ polyomavirus particles incapable of expressing a functional small T antigen and therefore incapable of replicating in large T antigen-deficient cells which are permissive for the wild type polyomavirus.

Cell lines for use in this invention may be conventional mammalian cell lines permissive for a polyomavirus that are genetically modified so that they express a functional polyomaviral large T antigen and do not express a functional polyomaviral small T antigen. Cell lines according to the invention may advantageously be used for the production of recombinant proteins since they are able to replicate circular DNA molecules harbouring the polyomavirus origin of replication.

The invention also relates to a composition as described above for use as a medicament.

DETAILED DESCRIPTION OF THE INVENTION

The present inventor has found that the large T antigen of a polyomavirus on its own promotes expression of the polyomaviral capsid proteins and that the polyomaviral small T antigen is not required for that purpose. This means that in the absence of polyomaviral T antigens in cells, the SVEP is a constitutive but weak promoter, compared to other viral promoters such as the cytomegalovirus (CMV) immediate early promoter, whereas the SVLP is shut-off at the transcriptional or post-transcriptional level. Surprisingly, in SV40-permissive cells, the SV40 large T antigen on its own was found to be capable of sustaining the multiplication of SV40 viral vector DNA and of activating SVLP, leading to the accumulation of capsid proteins and resulting in the efficient production of SV40 viral vector particles.

In the prior art, SV40 strains have been generated that are deficient in encoding the small T antigen. Gauchat et al. (Nucleic Acids Research 14: 9339-9351, 1988) describe an SV40 deletion mutant dl883 that lacks the small T antigen but produces a functional large T antigen in infected cells. When this mutant virus strain was used to infect monkey kidney cells and CV-1 cell cultures, the mutant virus strain was less efficient in inducing large T antigen-mediated cell division and subsequent virus replication than wildtype SV40. The authors concluded that the small T antigen has a helper function, assisting the large T antigen in inducing cell division and virus replication. This prior art thus teaches away from the present invention, since it shows that compared to cells infected with wildtype SV40, many cells infected with dl883 do not divide and do not produce virus particles. The absence of small T antigen in a cell is taught to be detrimental to viral vector production.

The Gauchat et al. publication is inconclusive on whether virus particles are produced or not. They merely measure the production of virus DNA in cells, which is not equivalent to the production of intact virus particles.

The present invention is therefore contra-intuitive for a skilled person. Moreover, it is known to a skilled person that the small T antigen is an effective inhibitor of RNAi. Since RNAi is known to serve as an antiviral mechanism, it would be expected that a decrease in the amount of intracellular small T antigen leads to an increase in the RNAi-based antiviral activity, resulting in a reduced production of virus particles. The inventors surprisingly found that the opposite is true. When the large T antigen is provided in trans, i.e. the cell line produces the large T antigen, wherein both the cell line and the polyomavirus strain lack a functional small T antigen, polyomavius particles are produced in high amounts. The difference between the present invention and the results of Gauchat et al. is that in the experiments described in Gauchat et al. a functional large T antigen is provided in cis, i.e. on the polyomaviral vector that replicates in the infected cell. This obviously leads to partial cell death and to a very inefficient viral vector production.

The present invention provides methods for the replication of recombinant polyomaviral vector particles and polyomaviral vector packaging cell lines and cell lines that support replication of polyomaviral replicons said polyomaviral vectors and replicons being incapable of expressing a functional polyomaviral small T antigen.

In the present invention all cells contribute to the polyomaviral vector production and levels of $1 \times 10^6$ or even $1 \times 10^{11}$ viral vector particles per milliliter cell culture volume may be obtained in a method according to the invention.

The expression "functional large T antigen" or "functional parts thereof" in this context means a large T antigen or a fragment or analogue thereof obtainable from a polyomavirus that is capable of performing the same function as that required for performing the invention as attributable to the large T antigen from which they are derived, more in particular, capable of sustaining the multiplication of polyomaviral viral vector DNA and of activating the SVLP in cells permissive for the polyomavirus.

The functionality of large T antigen can be tested by co-expressing an expression plasmid coding for polyomavirus large T antigen or a fragment or analogue thereof together with T antigen-deleted polyomaviral vector DNA in cells permissive for the wildtype polyomavirus and determining whether polyomavirusl vector particles are produced. It may be concluded that polyomavirus large T antigen or a fragment or analogue thereof is a functional large T antigen if a single polyomavirus particle is produced in this assay. Such may be determined by electron microscopy or any other suitable method known in the art.

The expression "functional small T antigen" or "functional parts thereof" in this context means a small T antigen or a fragment or analogue thereof obtainable from a polyomavirus that is capable of performing the same function as that required for performing the invention as attributable to the large T antigen from which they are derived, more in particular, capable of interacting with and/or inhibiting protein phosphatase 2A. The functionality of small T antigen can be tested using a binding assay between a polyomaviral small T antigen or a fragment or analogue thereof and protein phosphatase 2A as described by CHO U.S. et al., PLoS Biology 5(8): e202, 2007. It may be concluded that the small T antigen or a fragment or analogue thereof is a functional small T antigen when the interaction and/or inhibition in this assay is above background.

The cell lines useful in the present invention may express polyomaviral large T antigen or functional parts thereof and are incapable of expressing functional polyomaviral small T antigen. As a consequence the cell lines of the invention do not accumulate the polyomavirus-encoded T antigen oncoproteins and replication competent wildtype polyomaviruses cannot emerge from cells of the invention by recombination between the polyomaviral vector and the chromosomally inserted polyomaviral large T antigen sequences.

A cell line for use in the present invention may be obtained by the skilled person using his ordinary skills. In addition, he may follow the guidance provided in the examples in order to arrive at a cell line for use in the invention.

It is also an object of the present invention to provide a polyomavirus permissive cell line, preferably a primate cell line or even more preferred a simian cell line such as a Vero cell line (ref African Green Monkey kidney cell line ECACC 88020401 European Collection of Cell Cultures, Salisbury, Wiltshire, UK) comprising a gene encoding functional polyomaviral large T antigen or a functional fragment thereof, the gene sequence being incapable of expressing a functional polyomaviral small T antigen, for instance by deleting small T antigen-specific sequences. Said cell line is capable of multiplying and packaging T antigen-deleted polyomavirus vectors.

The skilled addressee will appreciate that the recombinant polyomaviral vectors, such as SV40 vectors, which are produced in the cell lines of the invention may not comprise T antigen-specific gene sequences and thus will be incapable of replicating in a mammalian cell lacking large T antigen. The exemplified T antigen-deleted SV40 replicons appeared to replicate at a high rate in the production cell lines of the invention.

The term "nucleotide sequence homology" as used herein denotes the presence of homology between two polynucleotides. Polynucleotides have "homologous" sequences when either a sequence of nucleotides in the two polynucleotides is the same or when a sense sequence of the one and an antisense sequence of the other polynucleotide is the same when aligned for maximum correspondence. Sequence comparison between two or more polynucleotides is generally performed by comparing portions of at least two sequences over a comparison window to identify and compare local regions of sequence similarity. The comparison window is generally from about 20 to 200 contiguous nucleotides in length. The "percentage of sequence homology" for polynucleotide sequences of the invention, such as 50, 60, 70, 80, 90, 91, 92, 93, 94, 95, 96, 97, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F., Journal of Molecular Biology 215: 403, 1990; Altschul, S. F. et al., Nucleic Acid Research 25: 3389-3402, 1997) and ClustalW programs both available on the internet. Other suitable programs include GAP, BESTFIT and FASTA in the Wisconsin Genetics Software Package (Genetics Computer Group (GCG), Madison, Wis., USA).

The homology between nucleic acid sequences may be determined with reference to the ability of the nucleic acid sequences to hybridise to each other upon denaturation (e.g., under conditions of 400 mM NaCl, 40 mM PIPES pH 6.4, 1 mM EDTA, at a temperature of 50 degrees Celsius to 65 degrees Celsius and hybridisation for 12-16 hours, followed by washing) (Molecular Cloning: a Laboratory Manual: 2nd edition, Sambrook et al., Cold Spring Harbor Laboratory Press, 1989 or Current Protocols in Molecular Biology, Second Edition, Ausubel et al. eds., John Wiley & Sons, 1992).

Generally speaking, those skilled in the art are well able to construct polyomavirus vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al., Cold Spring Harbor Laboratory Press, 1989.

The term "heterologous" is used broadly throughout to indicate that the nucleic acid sequence, polynucleotide sequence, gene or sequence of nucleotides in question have been introduced into said polyoma viral vector producer cell line, using genetic engineering, i.e. by human intervention. A heterologous gene may in principle replace an endogenous equivalent gene, or be additional to the endogenous genes of the genome of the host cell or polyoma virus i.e. is non-naturally occurring in cells of the host species or in polyoma viruses.

By "promoter" is meant a DNA sequence from which transcription may be initiated of DNA operably linked downstream (i.e. in the 3' direction on the sense strand of double stranded DNA). "Operably linked" means joined as part of the same nucleic acid molecule, suitably positioned and oriented for transcription to be initiated from the promoter. DNA operably linked to a promoter is "under transcriptional initiation regulation" of the promoter.

The promoter may be a constitutive promoter, an inducible promoter or tissue-specific promoter. The terms "constitutive", "inducible" and "tissue-specific" as applied to a promoter is well understood by those skilled in the art. The promoter is preferably derived from viruses, including 5'-long terminal repeats from retroviruses and lentiviruses, the cytomegalovirus immediate early promoter (CMVie), the human elongation factor 1 alpha promoter (EF-1alpha) and the like. Such promoters are readily available and are well known in the art.

By "polyadenylation signal" is meant a sequence of nucleotides from which transcription may be terminated and a poly-A tail is added to the transcript. As polyadenylation signal any polyadenylation signal applicable in human or animal cells can be used.

A cell line according to the invention may be derived from any suitable cell line known in the art such as MDCK, PER.C6, HEK293, CV1 and the like, but is preferably a Vero or CHO cell line.

A suitable cell line according to the invention is a polyomavirus permissive cell line incapable of expressing the polyomaviral small T antigen and preferably comprises the following genetic elements:
i) the polyomaviral large T antigen coding domain or part thereof, and optionally
ii) a selectable marker such as a neomycin resistance gene, puromycin resistance gene, hygromycin resistance gene or other marker.

Such a cell line may be devoid of the large intron of the polyomavirus early transcript harbouring small T antigen-specific DNA sequences The cell line in a preferred embodiment may include a transcriptional enhancer sequence stably integrated into the chromosomal DNA of the cell line, such that it may be further selected on the basis of the activity of the transcriptional enhancer. Such markers and such selection procedures are well known in the art.

Different polyomaviral vector production cell lines, eg SV40 viral vector producer cell lines, may be generated by transfecting the cells with different vectors, such as plasmids, depending on their pedigree. The methodology for transfection of cell lines is well known in the art. For example, the Vero cell line is widely used for the production of virus particles for vaccines. This has found many applications in prophylaxis of viral diseases.

A suitable cell line may be obtained by transfection with a first plasmid comprising the following components
i) the polyomaviral large T antigen coding domain or part thereof, devoid of the large intron of the polyomavirus early transcript harbouring small T antigen-specific sequences and optionally
ii) a selectable marker such as a neomycin resistance gene, puromycin resistance gene, hygromycin resistance gene or other marker.

Thus a single vector or plasmid could carry both the polyomaviral large T antigen coding domain and a selectable marker sequence. It is also possible that two separate DNA carrying vectors or plasmids are utilized, one carrying the polyomaviral large T antigen coding domain and a second carrying the selectable marker, depending on design. Any further genetic elements that may be needed to confer a polyomaviral vector production capability on a producer cell line may also be placed onto one or more DNA vectors or plasmids that may then be used to transfect the production cell line of choice. For instance, the Vero production cell line does not already contain polyomaviral T antigen sequences in it, so the large T antigen coding domain may be added into it, and the resulting nascent producer cells harbouring the large T antigen coding domain in them may then be selected for, by using a selectable marker system.

The invention now permits for the first time the preparation of compositions comprising recombinant polyomaviral vectors in sufficient amounts for therapeutic purposes, without the risk of contamination with wildtype polyomaviruses that occur from recombination between polyomaviral vector DNA and host cell DNA. This phenomenon is well described in the literature (Gluzman Y., Cell 23: 175-182, 1981; Oppenheim A. and Peleg A., Gene 77: 79-86, 1989; Vera M. et al., Molecular Therapy 10: 780-791, 2004).

The frequency with which this recombination occurs is less well documented however. The estimates vary greatly. Shaul et al estimated that recombination could occur with a frequency of at least $10^{-6}$ (Shaul et al., Proc. Natl. Acad. Sci. USA 82: 3781-3784, 1985), whereas more recent estimates show a much higher recombination rate, in the order of $10^{-3}$ (Arad et al., Virology 304: 155-159, 2002).

A complicating factor in estimating the frequency of recombination is that the wildtype polyomavirus replicates faster than the recombinant polyomaviral vector lacking the genes encoding functional T antigens.

Therefore we established the maximum number of recombinant SV40 vector particles that could be produced in a conventional cell culture according to the prior art, without the appearance of any wild type revertants.

Therefore, we infected COS-1 cells with recombinant SV40 vector particles according to a standard protocol (Vera M. et al., Molecular Therapy 10: 780-791, 2004) and calculated the maximum number of viral vector particles that could be produced without the occurrence of a single detectable genome of the wildtype virus as detected by a very sensitive quantitive PCR assay.

It was found that up to $1 \times 10^4$ viral vector particles could safely be produced without the occurrence of a detectable amount of wildtype revertants in the majority of experiments performed. A significant number of preparations comprising $1 \times 10^5$ viral vector particles however, was positive for wildtype revertants, whereas all of the preparations comprising $1 \times 10^6$ viral vector particles were contaminated with wildtype viruses and thus unsafe for medical use.

The fact that the polyomaviral vector preparations according to the prior art are unsafe for medical use is underlined by the fact that the wildtype SV40 particles in the preparations comprising more than $1 \times 10^6$ recombinant SV40 vector particles were able to infect SV40-permissive cells in vitro when tested according to a method of the prior art as described by Katzman R. B. et al., (Journal of Virological Methods 150: 7-13, 2008).

The invention now allows for the first time the preparation of a composition comprising more than $1 \times 10^6$ polyomaviral vector particles without any wildtype polyomavirus particles being present in the composition. The invention therefore relates to composition comprising more than $1 \times 10^6$ polyomaviral vector particles incapable of expressing a functional polyomaviral small T antigen and incapable of replicating in cells which are permissive for the wildtype polyomavirus. Such preparations may advantageously contain $1 \times 10^7$ vector particles or more, such as up to $1 \times 10^8$, $1 \times 10^9$, $1 \times 10^{10}$, or $1 \times 10^{11}$ vector particles or more.

The expression "incapable of replicating in cells which are permissive for the wildtype polyomavirus" means that the composition does not contain a single wildtype revertant polyomavirus particle among the at least $1 \times 10^6$ polyomaviral vector particles. This may be measured either by the quantitative PCR assay as described by Vera M. et al., Molecular Therapy 10: 780-791, 2004, or by infecting a cell line permissive for the wildtype polyomavirus present in the composition. In the latter case the absence of a single plaque in the plaque assay (Katzman R. B. et al., Journal of Virological Methods 150: 7-13, 2008) indicates the absence of a single wildtype polyomavirus particle.

In a preferred embodiment, the preparation according to the invention relates to a composition comprising a primate polyomavirus, such as a simian polyomavirus, more in particular an SV40, Simian virus 12 (SV12), Lymphotropic polyomavirus, African green monkey polyomavirus or Chimpanzee polyomavirus. Cell lines permissive for the primate polyomavirus are preferably selected from the group consisting of Vero cells, CV1 cells, PerC.6 cells, HEK293 cells and the like.

In another embodiment, the preparation according to the invention relates to a composition comprising a rodent polyomavirus such as mouse or hamster polyomavirus, more in particular a Murine polyoma virus or Hamster polyomavirus. Cell lines permissive for the mouse or hamster polyomavirus are preferably selected from the group consisting of CHO cells and the like.

The present invention also discloses the generation of vector production cell lines for the production of recombinant polyoma viral vector particles that are safe for medical use.

Accordingly, the invention relates to a cell line permissive for a polyomavirus, said cell line being capable of expressing a functional large T antigen and incapable of expressing a small T antigen. Such a cell line adequately supports the safe production of recombinant polyomaviral vector particles without the risk of obtaining wild type revertant polyomavirus particles since the cells lack any homologous sequences between the chromosomal DNA of the cell and the recombinant polyomavirus DNA. The gene encoding the large T antigen is preferably stably integrated in the genome of the cell.

The term "recombinant polyomaviral vector" in this context is to be interpreted as a polyomavirus incapable of expressing a functional polyomaviral large T antigen, preferably incapable of expressing a functional large and small T antigen. Such a recombinant viral vector may for instance lack the coding sequence for either the large T antigen or both the large T and the small T antigen.

The expression "permissive for a polyomavirus" in this context means that that the cell line supports the replication of polyomavirus particles upon infection with the polyomavirus or upon the introduction of polyomavirus DNA by transfection or other means of delivering DNA into a cell.

In another aspect, the invention provides a method for producing recombinant polyomavirus particles incapable of expressing a functional small T antigen comprising the steps of a. Providing a cell line permissive for a wildtype polyomavirus, said cell line being capable of expressing a functional polyomaviral large T antigen and incapable of expressing a functional small T antigen, b. Introducing into said cell line a polyomavirus DNA incapable of encoding a functional small T antigen, c. Culturing said cells in a growth medium under conditions allowing the formation of polyomavirus particles and d. Harvesting the recombinant polyomavirus particles from the cell culture.

In a preferred embodiment, the polyomavirus DNA is introduced into the cell by transfection of the DNA.

In further aspects of the invention there is provided a pharmaceutical composition for the treatment of an individual suffering from a disease. The pharmaceutical composition may comprise a therapeutically effective amount of one or more polyomavirus vectors such as SV40, prepared according to a process of the invention and a pharmaceutically acceptable carrier or diluent. The pharmaceutical compositions of the invention can be formulated in any suitable form for administration to the individual in need thereof. Such formulations may be in any form for administration such as topical, oral, parenteral, intranasal, intravenous, intramuscular, intralymphatic, subcutaneous, intraocular or even transdermal administration.

The pharmaceutical compositions of the invention generally comprise a buffering agent, an agent that adjusts the osmolarity thereof, an optionally, one or more pharmaceutically acceptable carriers, excipients and/or additives as known in the art. Supplementary active ingredients may also be incorporated into the compositions of the invention. The carrier may be a solvent or dispersion medium containing, for example, water, ethanol, polyol (for example, glycerol, propylene glycol, and liquid polyethylene glycol, and the like), suitable mixtures thereof, and vegetable oils. The correct fluidity may be maintained by the use of a coating, such as lecithin, by the maintenance of the required particle size in the case of dispersion and by the use of surfactants.

The invention will now be further described with reference to the following examples.

EXAMPLES

Example 1

Construction of the SV40 Derived Gene Delivery Vector

Six oligonucleotides were designed:
WdV101: CCGCTCGAGTTGCGGCCGCTGTGCCTTCTAGTTGCCAGCCATC (SEQ ID No. 1) (containing a XhoI and a NotI restriction site) and
WdV102: GGTACCATAGAGCCCACCGCATCCCAGCATGCC (SEQ ID No. 2) (containing a KpnI restriction site) and
WdV103: GGCCGCTTTATTAATTAAGCCCTGCAGGTTGTTTAAACTTGGCGC GCCTTAT (SEQ ID. No. 3) (contains from 5' to 3' subsequently a NotI sticky restriction site, a PadI, SbfI, PmeI and an AscI intact restriction site and a ClaI sticky restriction site) and
WdV104: CGATAAGGCGCGCCAAGTTTAAACAACCTGCAGGGCTTAATTAAT AAAGC (SEQ ID No. 4) (contains from 3' to 5' subsequently a NotI sticky restriction site, a PadI, SbfI, PmeI and an AscI intact restriction site and a ClaI sticky restriction site) and
WdV105: CGGGATCCAGACATGATAAGATACATTG (SEQ ID NO. 5) (containing a BamHI restriction site) and
WdV106: ATAGTTTAGCGGCCGCAACTTGTTTATTGCAGCTTATAATGG (SEQ ID No. 6) (containing a NotI restriction site).

Purified plasmid DNA of the SV40 vector pSL-PL (De La Luna, S. et al., Journal of General Virology 74: 535-539, 1993) was subjected to PCR using oligonucleotides WdV105 and WdV106. The resulting amplified DNA fragment comprised the SV40-polyadenylation signal flanked by a BamHI restriction site at the 5' end and a NotI restriction site at the 3' end. This SV40 polyadenylation signal fragment was digested with BamHI and NotI and the resulting 150 bp long DNA fragment was isolated from an agarose gel and cloned into a likewise digested pBluescript SK− plasmid (Promega), yielding pAM002.

Purified pEF5/FRT/5-DEST (Invitrogen) plasmid DNA was subjected to PCR using oligonucleotides WdV101 and WdV102. The resulting amplified DNA fragment comprising the bovine growth hormone (BGH) polyadenylation signal flanked by subsequently a XhoI and a NotI restriction site at the 5' end and an KpnI restriction site at the 3' end. This BGH polyadenylation signal fragment was digested with KpnI and NotI, and the resulting 250 bp long DNA fragment was isolated from an agarose gel and ligated into the likewise digested pAM002 plasmid. Transformation with this ligation mixture was performed in a methylation insensitive E. coli strain. This resulted in plasmid pAM003.

The two complementary oligonucleotides WdV103 and WdV104 were annealed by incubating them in a water bath that was cooling down autonomously from boiling temperature to room temperature, yielding a DNA linker containing subsequently a NotI sticky restriction site, a PadI, SbfI, PmeI and a AscI intact restriction site and a ClaI sticky restriction site. This linker was ligated into the pAM002 plasmid that was digested with NotI and ClaI and isolated from an agarose gel. The ligation mixture was subsequently used to transform a methylation insensitive E. coli strain, yielding pAM004.

Purified plasmid DNA of the SV40 vector pSL-PL was digested with ClaI and BamHI. The resulting 2.6 kb DNA fragment that contains the SV40 origin and the SV40 late region is purified from agarose and cloned into likewise digested pAM004. This resulted in the new SV40 vector plasmid pAM005.

Example 2

Molecular Cloning of a SV40 Luciferase Expression Vector and the Production of Recombinant SV40 Luciferase Vector Particles The expression plasmid pGL3 (Promega) was used as template for cloning of the firefly luciferase using PCR. Two oligonucleotides were designed WdV389: 5'-TTGGCGCGCCATGGAAGACGCCAAAAACATAAAGAAAGGC-3' (SEQ ID NO: 7) and WdV407: 5'-CCCTTAATTAATTACACGGCGATCTTTCCGCCCTTC-3' (SEQ ID NO: 8) containing respectively restriction sites AscI and PacI. The PCR amplified luciferase fragment was subsequently AscI and PacI digested and ligated into pAM005, resulting in pAM006.

Two oligonucleotides were designed WdV437 5' GGGATCCAGACATGATAAGATACATTG 3' (SEQ ID NO: 9) and WdV442: ATAGTTTAGCGGCCGCAATGAATGCAATTGTTGTTGTTAACTTG (SEQ ID NO: 10) containing respectively BamHI and NotI restriction site. The pSL-PL vector was used as template for cloning of the large T antigen trailer sequence using PCR. The resulting PCR fragment was digested with BamHI and NotI and cloned into the BamHI and NotI (partially digested) pAM006, resulting in pAM020.

Recombinant SV40 vector particles encoding the firefly luciferase (SV-Luc) were produced according Vera M. et al., Molecular Therapy 10: 780-791, 2004. COS-1 cells were transfected with NotI-digested and recircularized pAM020 DNA and three days after transfection crude lysates were prepared from the cell culture by repeated freeze-thawing. The SV-Luc vector particles were amplified in one round in COS-1 cells growing in a T175 flask. The SV-Luc vector particles were finally concentrated and purified from the crude lysate by sucrose gradient ultracentrifugation, yielding a vector stock with $5 \times 10^{11}$ SV-Luc genome copies per milliliter cell culture.

Example 3

Construction of an Expression Plasmid Encoding the SV40 Large T Antigen

A synthetic multiple cloning site (MCS) was designed containing restriction sites for NotI, PacI, SbfI, PmeI, AscI and ClaI. Two oligonucleotides were designed WdV436: 5'-GCCGCTTTATTAATTAAGCCCTGCAGGTTGTTTAAACTTGGCGCGCCTTAT-3' (SEQ ID NO: 11) and WdV437: 3'-CGATAAGGCGCGCCAAGTTTAAACAACCTGCAGGGCTTAATTAATAAAGC-5'. (SEQ ID NO 12). Both oligonucleotides WdV436 and WdV437 were annealed to each other and ligated into pBluescript SK− (Promega), yielding the recombinant plasmid pAM007.

Two oligonucleotides were designed to introduce an additional NotI restriction site WdV452: CGGCGGCCGCGTAC (SEQ ID NO: 13) and WdV453: GCGGCCGC. Both oligonucleotides were annealed and ligated into pAM007, yielding the recombinant vector pAM008.

The expression vector pLenti6.3/V5DEST_verA (Invitrogen) was used as a template for cloning of the cytomegalovirus immediate early (CMVie) promoter using PCR. Two oligonucleotides were designed WdV286: 5'-TTG-GCGCGCCTCAATATTGGCCATTAGCCATATTATTCAT-TGG-3' (SEQ ID NO: 14) and WdV220: 3'-GACAAGCT-TCCAATGCACCGTTCCCGGCCGCGGAGGCTGGA TCG-5' (SEQ ID NO: 15) flanking the CMV promoter. Oligonucleotides WdV286 and WdV220 contained restriction sites AscI and HindIII respectively. Subsequently, purified pLenti6.3/V5DEST_verA was subjected to PCR using oligonuleotides WdV286 and WdV220, yielding a CMV promoter DNA fragment. This fragment was AscI and HindIII digested and ligated into pBluescript SK−, yielding pAM009.

The expression vector pGL4.22 (Promega) was used as a template for cloning of the puromycin N-acetyltransferase antibiotic resistance gene using PCR. Two oligonucleotides were designed WdV454: 5'-CCACCCAAGCTTATGAC-CGAGTACAAGCCCACGGTGCG-3' (SEQ ID NO: 16) and WdV455: 3'-TATCCGCTCGAGTCAGGCAC-CGGGCTTGCGGGTCATGC-5' (SEQ ID NO: 17) flanking the puromycin N-acetyltransferase antibiotic resistance gene and containing restriction sites HindIII and XhoI, respectively. Plasmid pGL4.22 was subjected to PCR using oligonucleotides WdV454 and WdV455, yielding the puromycin N-acetyltransferase cDNA. This fragment was HindIII and XhoI digested and ligated into pAM009, yielding pAM010.

The expression vector pEF5/FRT/5-DEST (Invitrogen) was used as a template for cloning of the BGH polyadenylation signal using PCR. Two oligonucleotides were designed WdV456: 5'-CAACCGCTCGAGCTGTGCCT-TCTAGTTGCCAGCCATC-3' (SEQ ID NO: 18) and WdV457: 3'-CGGGGTACCCCATAGAGCCCACCG-CATCCCC-5' (SEQ ID NO: 19) flanking the polyadenylation signal and containing restriction sites XhoI and KpnI respectively. Plasmid pEF5/FRT/V5-DEST was subjected to PCR using oligonucleotides WdV456 and WdV457, yielding the BGH polyadenylation signal cDNA. This fragment was XhoI and KpnI digested and ligated into pAM010, yielding pAM011.

Plasmids pAM008 was digested with AscI and PmeI and the DNA fragment comprising the puromycin N-acetyltransferase coding domain was purified from an agarose gel and ligated into pAM008, yielding pAM012.

DNA of a full-length SV40 DNA clone (ATCC number VRMC-2) was used as template for cloning of the SV40 T antigen coding region using PCR. Two oligonucleotides were designed WdV408: ACCATGGATAAAGTTT-TAAACAGAGAGGAATCTTTGCAGC (SEQ ID NO: 20) containing an attB1 recombination site and WdV409: TTAT-GTTTCAGGTTCAGGGGGAGGTGTGGGAGG (SEQ ID NO: 21) containing an attB2 recombination site. WdV408 and WdV409 were used to PCR amplify the genomic T antigen coding region. Subsequently, a gateway entry clone was generated from the generated DNA fragment and pDONR221, resulting in pAM013. A T antigen expression plasmid was generated by gateway recombination between pAM013 and pEF5/FRT/V5-DEST, resulting in pAM014.

The NotI and PmeI restriction sites in plasmid pAM014 were eliminated by NotI and PmeI digestion of pAM014 followed by a T4 DNA polymerase treatment and re-ligation, yielding pAM015. The T antigen expression cassette was subsequently isolated by a SphI digestion followed by a T4 DNA polymerase treatment and a NruI digestion.

In order to generate a shuttle plasmid two oligonucleotides were designed WdV448: TCCTGCAGGCGGGGTACCCTAGTCTAGACTAGC-CGCGGGGAGTTTAAACAGCT (SEQ ID NO: 22) and WdV449: GTTTAAACTCCCCGCGGCTAGTCTAGACTAGGG-TACCCCGCCTGCAGGAGTAC (SEQ ID NO: 23). Oligonucleotides WdV448 and WdV449 were annealed generating a DNA fragment that contains the KpnI, SbfI, KpnI, XbaI, SacII, PmeI and SacI restriction sites. This DNA fragment was ligated into KpnI and SacI digested pBluescript SK− (Promega), yielding pAM016. Plasmid pBluescript SK− was digested with KpnI and XbaI and the MCS DNA fragment was isolated from an agarose gel. The MCS DNA fragment was ligated into pAM016 digested with KpnI and XbaI, resulting in pAM017.

The EF1 alpha driven T antigen expression cassette from pAM015 was isolated by a NruI and SphI digest followed by a T4 DNA polymerase treatment. The resulting DNA fragment was cloned into pAM017 digested with EcoRV, resulting in pAM018.

Plasmid pAM018 was digested with SbfI and PmeI and the DNA fragment comprising the T antigen expression cassette was isolated from an agarose gel and cloned into pAM012 digested with SbfI and PmeI, resulting in pAM019.

Four oligonucleotides were designed WdV487: 5'-GCA-GGCTACCATGGATAAAGTTTTAAACAGAGAG-3' (SEQ ID NO: 24) and WdV490: 3'-CCATTCATCAGTTC-CATAGGTTGGAATCTCAGTTGCATCCCAGAAGC-CTCCAAAG-5' (SEQ ID NO: 25) WdV:489 5' CTTTG-GAGGCTTCTGGGATGCAACTGAGATTCCAACCTAT GGAACTGATGAATGGG-3' (SEQ ID NO: 26) and WdV488: 5'-AGGAATGTTGTACACCATGCATTT-TAAAAAGTC-3'(SEQ ID NO: 27).

Oligonuleotides WdV487 and WdV490 and oligonucleotides WdV489 and WdV488 were used to amplify the first and the second exon of the SV40 large T antigen respectively. Both generated DNA fragments were subsequently subjected to a fusion PCR using oligonucleotides WdV487 and WdV488.

The generated DNA fragment comprising the SV40 large T antigen coding region was digested with NcoI and NsiI and cloned into likewise digested pAM019, resulting in pAM001.

In summary, pAM001 contains an EF1 alpha promoter upstream of the large T antigen coding region and a CMVie promoter upstream of the puromycin N-acetyltransferase coding region.

Example 4

Generation of a Vero Producer Cell Line and Production of Recombinant SV40 Vector Particles Vero cells (Sigma-Aldrich order number: 88020401) were propagated and adapted to serum free culture DMEM medium (Invitrogen, product code: 41966-052). Adaptation to serum free conditions was performed by gradually reducing fetal bovine serum from 8, 6, 4, 2 and 0 percent in the medium each passage. From then the Vero-Serum Free (Vero-SF) cells were cultured in OptiPro SFM medium (Invitrogen) containing 2 percent L-glutamine at 37 degrees Celsius and 5 percent $CO_2$.

Vero-SF cells were transfected with pAM001 DNA using the transfection agent Exgen 500 (Fermentas, product code: R0511) according to the supplier's prescriptions. The transfected Vero-SF cells were subsequently selected for integration of the SV40 large T expression gene cassette into the chromosomal DNA by adding 2 µg/ml puromycine to the cell culture medium. Surviving colonies were isolated and propagated in OptiPro SFM medium containing 2 µg/ml puromycine and 2 percent L-glutamine. Puromycin-resistant cells were transferred OptiPro SFM medium containing 2 percent L-glutamine and 10 percent DMSO and stored at −156 degrees Celsius.

Example 5

Selection of SV40 High Producing SuperVero Subclones

Puromycin-resistant Vero clones transfected with pAM001 and VERO-SF control cells were cultured until they reached a confluence of 50 percent. The cell cultures were transduced with 50 µl of the SV-Luc vector stock containing approximately $2.5 \times 10^{10}$ vector genome copies.

Four hours post transduction the culture medium was replaced by fresh OptiPro SFM medium containing 2 µg/ml puromycine and 2 percent L-glutamine. Three days post transduction crude lysates are prepared from the transduced cells by freeze-thawing (Vera M. et al., Molecular Therapy 10: 780-791, 2004). COS-1 cells cultivated in DMEM supplemented with 10 percent fetal bovine serum (Invitrogen) were transduced with 100 microliters of crude lysate of each puromycin-resistant and pAM001-transfected Vero SF cell clone. Two days post transduction the COS-1 cells were subsequently tested for firefly luciferase expression as a measure for the amount of SV-Luc vector production in the corresponding puromycin-resistant and pAM001-transfected Vero SF cell clone. Cell clones that exhibited a comparable luciferase expression level to COS-1 cells were selected, propagated and expanded to create a cell bank. Cell clone Vero-SF001-86 was repeatedly monitored for SV-Luc production and produces similar amounts of recombinant SV40 vector particles as COS-1. A cell subclone of Vero-SF001-86 denoted Vero-SF001-86-01 was generated by limited dilution that repeatedly produces similar amounts of recombinant SV40 vector particles as the parental Vero-SF001-86 cell clone. Quantitative PCR according to Vera M. et al., Molecular Therapy 10: 780-791, 2004, revealed that cell clone Vero-SF001-86-01 denoted SuperVero routinely produces $1-10 \times 10^{11}$ vector genome copies per milliliter cell culture.

Example 6

Molecular Cloning of a Vector Used for Production of Recombinant Proteins in SuperVero Cells The SV40 origin of replication was PCR isolated from pTracer-SV40 (Invitrogen) and cloned into the firefly luciferase expression plasmid pGL3 (Promega resulting in expression vector pAM006. Subsequently, SuperVero cells were transfected with purified pAM006 and the control pGL3 expression vector DNA. Three days after transfection luciferase expression was measured. SuperVero cells transfected with pAM6 produced significantly more firefly luciferase compared to the control pGL3 transfected cells.

The invention claimed is:

1. Method for the production of recombinant polyomaviral vector particles not encoding a functional polyomaviral small T antigen, the method comprising:
   providing a non-human primate SV40 permissive cell or cell line,
      wherein the SV40 permissive cell or cell line comprises a gene encoding a functional polyomaviral large T antigen stably integrated into the genome of the cell; and
      wherein the SV40 permissive cell or cell line does not comprise a gene encoding a functional polyomaviral small T antigen,
   introducing into the SV40 permissive cell or cell line a polyomavirus DNA not encoding a functional polyomaviral small T antigen,
   culturing the cell or cell line in a growth medium under conditions allowing the formation of recombinant polyomaviral vector particles, and
   harvesting the recombinant polyomaviral vector particles from the cell culture.

2. A composition comprising recombinant polyomaviral vector particles not encoding a functional polyomaviral small T antigen produced by the method according to claim 1.

3. The composition of claim 2, wherein the composition comprises more than one million recombinant polyomaviral vector particles not encoding a functional polyomaviral small T antigen, the polyomaviral vector particles being incapable of replicating in cells that are permissive for the wildtype polyomavirus and do not express a functional polyomaviral large T antigen, wherein the composition does not contain a single polyomavirus particle being able to replicate in cells which are permissive for the wildtype polyomavirus wherein the cells do not express a functional polyomaviral large T antigen.

4. The composition of claim 3 wherein the polyomavirus is a primate polyomavirus.

5. The composition of claim 4 wherein the polyomavirus is a simian polyomavirus.

6. The composition of claim 5 wherein the polyomavirus is selected from the group consisting of SV40, SV12, Lymphotropic polyomavirus, African green monkey polyomavirus and Chimpanzee polyomavirus.

7. The composition of claim 6 wherein the polyomavirus is SV40.

8. The composition of claim 3, wherein the SV40 permissive cell or cell line is selected from the group consisting of Vero cells and CV1.

9. A non-human primate SV40 permissive cell or cell line, the cell or cell line comprising the recombinant polyomaviral vector particles of claim 2;
- wherein the cell or cell line comprises a gene encoding a functional polyomaviral large T antigen stably integrated into the genome of the cell; and
- wherein the cell or cell line does not comprise a gene a functional polyomaviral small T antigen.

10. A method for the production of a recombinant protein, the method comprising:
- utilizing the cell line of claim 9 to produce a recombinant protein.

11. The composition of claim 9, wherein the SV40 permissive cell or cell line is selected from the group consisting of Vero cells and CV1.

* * * * *